United States Patent [19]

Ukawa et al.

[11] Patent Number: 5,267,562
[45] Date of Patent: Dec. 7, 1993

[54] PULSE OXIMETER WITH PROBE DIFFERENCE COMPENSATION

[75] Inventors: Teiji Ukawa; Sunao Takeda; Hideo Ozawa, all of Tokyo, Japan

[73] Assignee: Nihon Kohden Corporation, Tokyo, Japan

[21] Appl. No.: 925,636

[22] Filed: Aug. 7, 1992

[30] Foreign Application Priority Data

May 28, 1992 [JP] Japan .................. 4-136710

[51] Int. Cl.$^5$ .................. A61B 5/00
[52] U.S. Cl. .................. 128/633; 356/41
[58] Field of Search .................. 128/633; 356/41

[56] References Cited

U.S. PATENT DOCUMENTS

| | | | |
|---|---|---|---|
| 4,621,643 | 11/1986 | New, Jr. et al. | 128/633 |
| 4,700,708 | 10/1987 | New, Jr. et al. | 128/633 |
| 4,770,179 | 9/1988 | New, Jr. et al. | 128/633 |
| 4,942,877 | 7/1990 | Sakai et al. | 128/633 |
| 5,058,588 | 10/1991 | Kaestle | 128/633 |

FOREIGN PATENT DOCUMENTS 59-64031 4/1984 Japan.
355129 8/1991 Japan.

Primary Examiner—Lee S. Cohen
Assistant Examiner—Kevin Pontius
Attorney, Agent, or Firm—Sughrue, Mion, Zinn, Macpeak & Seas

[57] ABSTRACT

A pulse oximeter of the present invention is to provide a greatly simplified in construction and a simplified procedure for performing arithmetic operations. The pulse oximeter of the present invention comprises a light-emitting diode which is provided in a probe and that illuminates a living tissue with red light of a reference wavelength, a light-emitting diode that illuminates the living tissue with infrared light, a light-receiving device that detects the optical output that remains after the living tissue absorbs the two wavelengths of red light and infrared light that have been issued from the light-emitting diodes, detectors which, on the basis of the detection output of the light-receiving device, compute the pulsating components of absorbances for the two wavelengths, a multiplier that multiplies the value from the detector by an appropriate coefficient in order to adjust that the value detected when using red light of a wavelength offset from the reference wavelength is gain-adjusted for correction to a known value obtained when using red light of the reference wavelength, a computing means that computes an absorbance ratio using both the value after gain adjustment that is delivered from the multiplier and the value from the detector, and a computing means that computes the oxygen saturation of arterial blood using the computed value. Information on the coefficient is provided by resistor which is built in the probe.

5 Claims, 3 Drawing Sheets

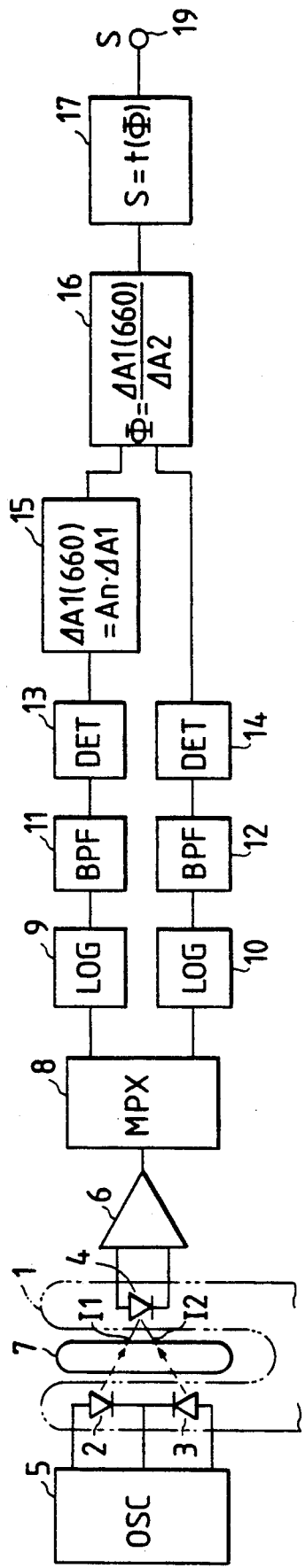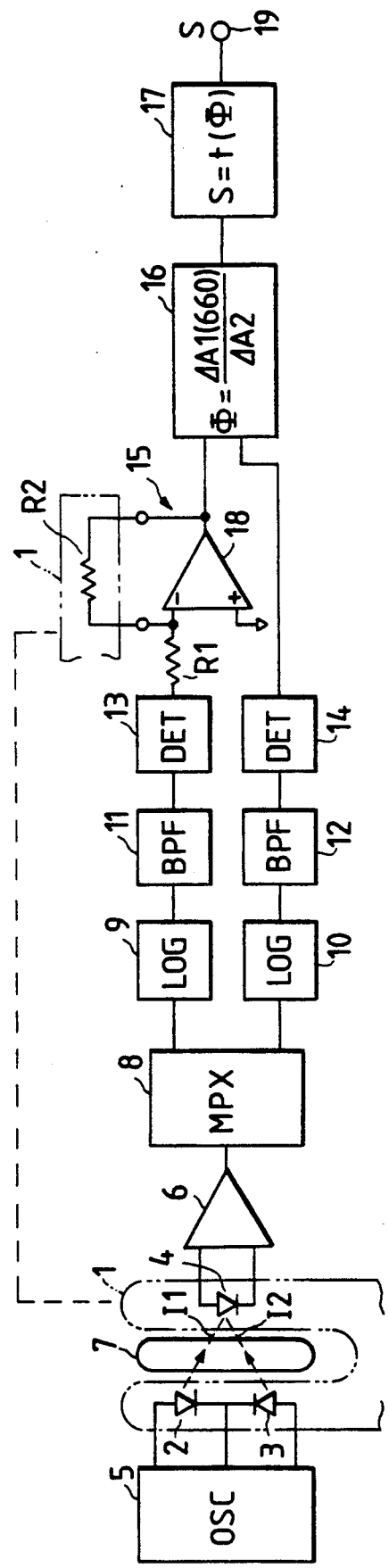

PULSE OXIMETER WITH PROBE DIFFERENCE COMPENSATION

BACKGROUND OF THE INVENTION

The present invention relates to a pulse oximeter for continuously measuring the oxygen saturation of the arterial blood of a subject in a bloodless manner by taking advantage of the difference in the characteristics of absorption by the organism of red light and infrared light emitting at different wavelengths. More particularly, the present invention relates to a pulse oximeter that permits simple correction of variations in the emission wavelength of the red LED that is provided in a probe.

A pulse oximeter is conventionally used to measure the oxygen saturation of arterial blood in a continuous and noninvasive manner. In actual measurement, the probe of the pulse oximeter is attached to the tip of a subject's finger or one of his earlobes and the living body of the subject is illuminated with red and infrared light at different wavelengths that are emitted from the probe at time intervals, and the oxygen saturation S of arterial blood is determined from the ratio $\phi$ between components of pulsation in absorbance as obtained from transmitted or reflected light for the two different wavelengths. A reference wavelength, say, 660 nm, is used for red light whereas a wavelength of 940 nm is typically used for infrared light. The probe contains in it two light-emitting diodes that emit at those two wavelengths and a single photodiode for light reception.

Suppose here that the absorbance of red light has a pulsating component $\Delta A1$ whereas the absorbance of infrared light has a pulsating component $\Delta A2$. The absorbance ratio $\phi$ for the two different wavelengths can be expressed by the following equation using $\Delta A1$ and $\Delta A2$:

$$\phi = \Delta A1/\Delta A2 \quad (A)$$

The oxygen saturation S is a function f of the absorbance ratio $\phi$ and is expressed as follows:

$$S = f(\phi) \quad (B)$$

The function f which correlates the oxygen saturation S to the absorbance ratio $\phi$ depends particularly on the wavelength of red light and the value of $\phi$ for the same value of oxygen saturation S varies with the wavelength of red light. FIG. 4 shows three characteristic curves for $\phi$ vs S at different wavelengths; curve U1 depicts the relationship at a wavelength of 660 nm; curve U2 plots the result obtained when the wavelength of red light is shifted to 650 nm; and curve U3 refers to the case where the wavelength is at 670 nm.

As is clear from those characteristic curves, if variations occur in the emission wavelength of the red LED contained in the probe, a certain correction must be made in order to measure the correct value of oxygen saturation S. This necessity presents no problem if the measurement is performed using the probe with which the pulse oximeter of interest is available since the necessary calibration has been completed for the oximeter. However, a problem arises if a different probe is to be attached to the main body of the oximeter for determining the oxygen saturation S.

Under the circumstances, there has been proposed an improved pulse oximeter of the type described in Unexamined Published Japanese Patent Application No. 64031/1984; the oximeter is so adapted that information on the emission wavelength of the red LED provided in the probe can be delivered from the probe to an external circuit to insure that the oxygen saturation S can be corrected by the main body of the oximeter on the basis of that wavelength information. Stated more specifically, the value of a certain wavelength is encoded and a resistor equivalent to the wavelength information for the red LED is mounted in the probe. The main body of the oximeter is so adapted that it is capable of reading the value of the resistor in terms of voltage, decoding the wavelength value, selecting an appropriate correction coefficient from a table that stores the values of red wavelength present for the main body and the correction coefficients necessary for calculating the oxygen saturation, and finally computing the correct value of oxygen saturation S.

FIG. 5 is a block diagram of a common pulse oximeter that uses the above-described prior art method of correction. A computing circuit 16 which is supplied with pulsating components of absorbances $\Delta A1$ and $\Delta A2$ for two wavelengths that have been detected with two detectors 13 and 14 and, using the values of $\Delta A1$ and $\Delta A2$, the absorbance ratio $\phi$ is computed in the computing circuit 16. The computed value of $\phi$ is sent to a computing circuit 17 in the next stage.

A probe 1 has a built-in resistor 20 that has encoded the information on the emission wavelength of a red LED 2. The value of the resistor 20 is read by a decoding portion 21 of the main body of the oximeter and converted to a value of wavelength, whereupon a correction coefficient corresponding to that value of wavelength is read out of a table 22 connected to the decoding portion 21. The table 22 is written in a ROM (read-only memory). The readout of the correction coefficient is set to the computing circuit 17, which uses both the value of absorbance ratio $\phi$ from the computing circuit 16 and the coefficient of correction to compute the oxygen saturation S that has been corrected for any variations in the emission wavelength of the red LED 2.

As described above, the conventional pulse oximeter which has the red LED 2 built in the probe 1 has seen it necessary to correct for any variations in the emission wavelength of that LED by equipping the probe 1 with the resistor 20 which encodes the value of said wavelength and which is equivalent to the wavelength information for the red LED. Another need has been to perform a decoding operation which consists of reading the value of the resistor 20 in the main body of the oximeter, thereby obtaining the value of the emission wavelength of the red LED. It has also been necessary to equip the main body with the table 22 storing those correction coefficients which are in one-to-one correspondence with the respective readout values of wavelength. All these factors have contributed to increasing the structural complexity of the pulse oximeter.

As for the table 22, a plurality of correction coefficients must be stored in consideration of the variations in the emission wavelength of the red LED 2 which is commercially available and, in a certain case, even those correction coefficients which are rarely used must be made available, thereby leading to complexity in the procedure for carrying out the decoding operation.

A further problem with the prior art pulse oximeter is that after an appropriate correction coefficient is selected on the basis of the wavelength information obtained from the probe 1, the correct value of oxygen saturation S must be determined using the selected coefficient but this only leads to complexity in the procedure for determining the oxygen saturation S.

SUMMARY OF THE INVENTION

The present invention has been accomplished in order to solve the aforementioned problems of the prior art and has as an object providing a pulse oximeter that is so designed as to avoid feeding wavelength information to the probe, whereby the need to perform encoding and decoding operations is eliminated to simplify not only the construction of the equipment but also the procedure for determining the oxygen saturation of arterial blood in subjects.

According to an aspect of the present invention, a pulse oximeter of the present invention comprises the following components:

a first light source that is provided in a probe to be attached to a subject and that illuminates a living tissue including an arterial blood flow with red light of a predetermined reference wavelength;

a second light source that is provided in said probe and that illuminates the living tissue including the arterial blood stream with infrared light;

a light-receiving device that detects an optical output that remains after the living tissue absorbs two wavelengths of red and infrared light that have been issued from said first and second light sources;

first computing means for, on the basis of a detection output of said light-receiving device, computing $\Delta A1$ and $\Delta A2$ which are pulsating components of absorbances for the two wavelengths due to the arterial blood stream;

gain adjusting means for multiplying a value of the output $\Delta A1$ from said first computing means by an appropriate coefficient An in order to adjust that a value of $\Delta A1$ corresponding to a component of pulsation in absorbance that is detected when using red light of a wavelength offset from said reference wavelength is gain-adjusted for correction to a known value of $\Delta A1$ that is obtained when using red light of said reference wavelength;

second computing means computing for an absorbance ratio $\phi$ by $\Delta A1/\Delta A2$ using both the value of $\Delta A1$ corresponding to the component of pulsation in absorbance after gain adjustment that is delivered from said gain adjusting means and $\Delta A2$ corresponding to the component of pulsation in absorbance for infrared light that is delivered from said first computing means; and third computing means for computing an oxygen saturation S of arterial blood using the absorbance ratio $\phi$ that is delivered from said second computing means.

In a preferred embodiment of the present invention, the gain adjusting means of the pulse oximeter is composed of a resistor that is provided in said probe to give information on the coefficient An and a multiplier to which said resistor is connected and which performs multiplication taking in the value of pulsation $\Delta A1$ that is delivered from said first computing means.

BRIEF DESCRIPTION OF THE DRAWINGS

FIG. 1 is a block diagram showing the basic construction of the pulse oximeter of the present invention;

FIG. 2 is a block diagram showing an embodiment of the pulse oximeter of the present invention;

DETAILED DESCRIPTION OF THE PREFERRED EMBODIMENTS

The basic concept of the present invention is described below.

Suppose that the wavelength of red light has a standard value of 660 nm and that the emission wavelength of the red LED 2 provided in the probe 1 has variations within certain limits (on the order of ±10 nm). If, as shown in FIG. 3, the ratio of pulsating components of absorbance $\phi$ at the wavelength 660 nm is written as $\phi(660)$ and $\phi$ at a certain wavelength as $\phi(n)$, then the relationship between $\phi(660)$ and $\phi(n)$ can be expressed by the following linear equation:

$$\phi(660) = An \cdot \phi(n) \tag{1}$$

Figure 3:
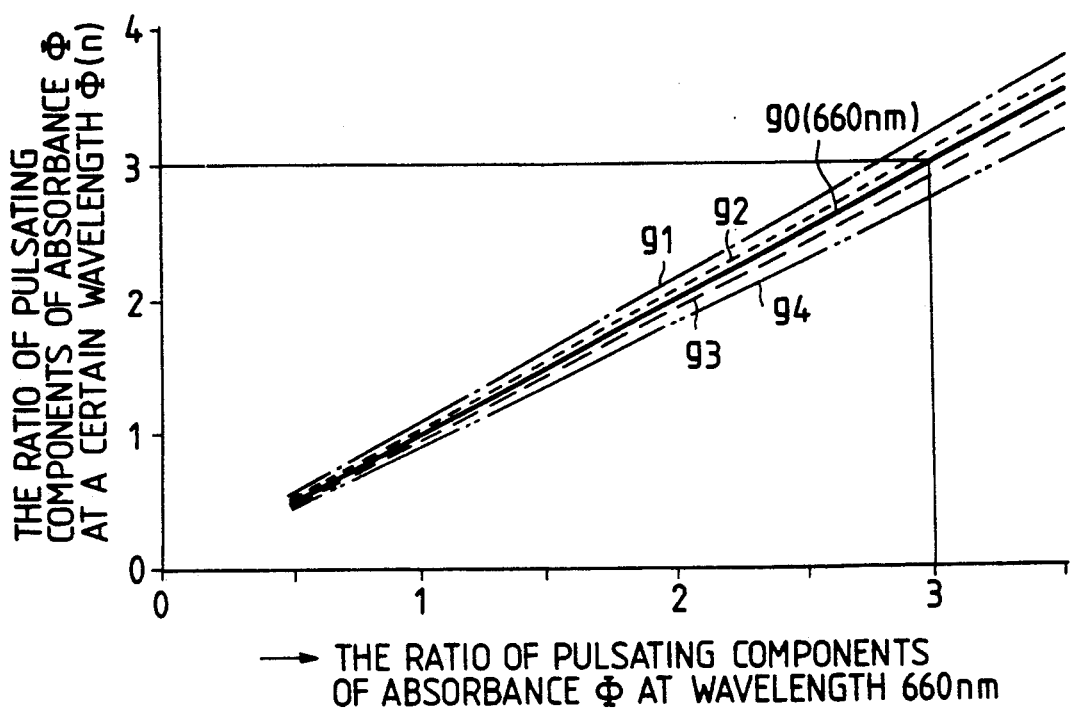
FIG. 3 is a graph showing how $\phi(660)$, or the absorbance ratio at the standard wavelength 660 nm, is related to $\phi(n)$ where n denotes a wavelength of red light that is offset from the standard value 660 nm.
Figure 4:
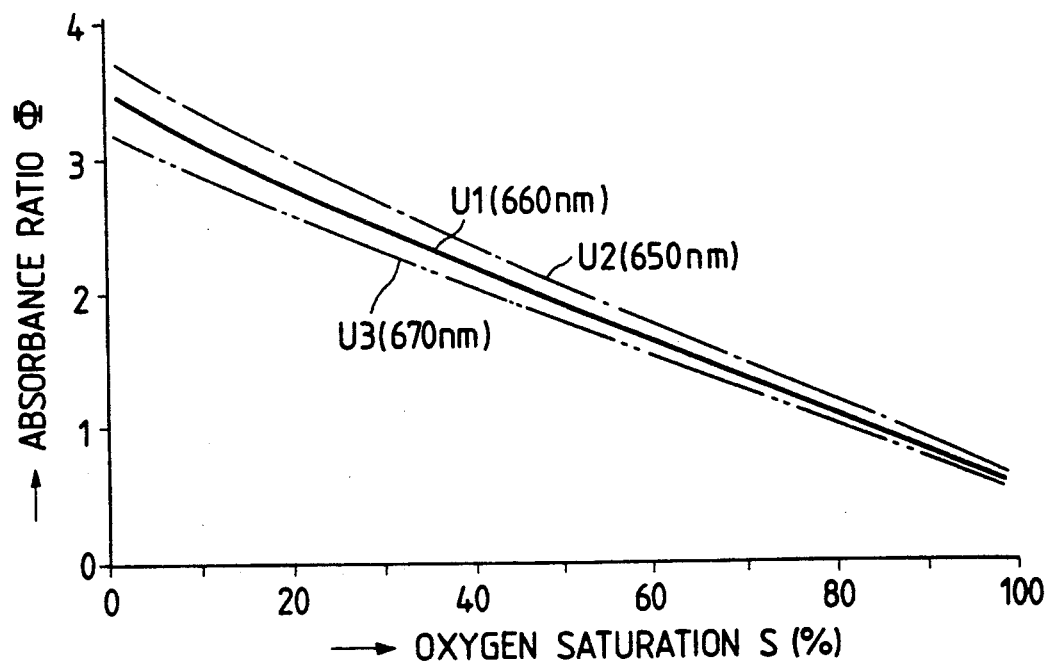
FIG. 4 is a characteristic diagram showing the relationship between the absorbance ratio $\phi$ for two wavelengths and the oxygen saturation S for three cases where the wavelength of red light is offset from the standard value 660 nm.
Figure 5:
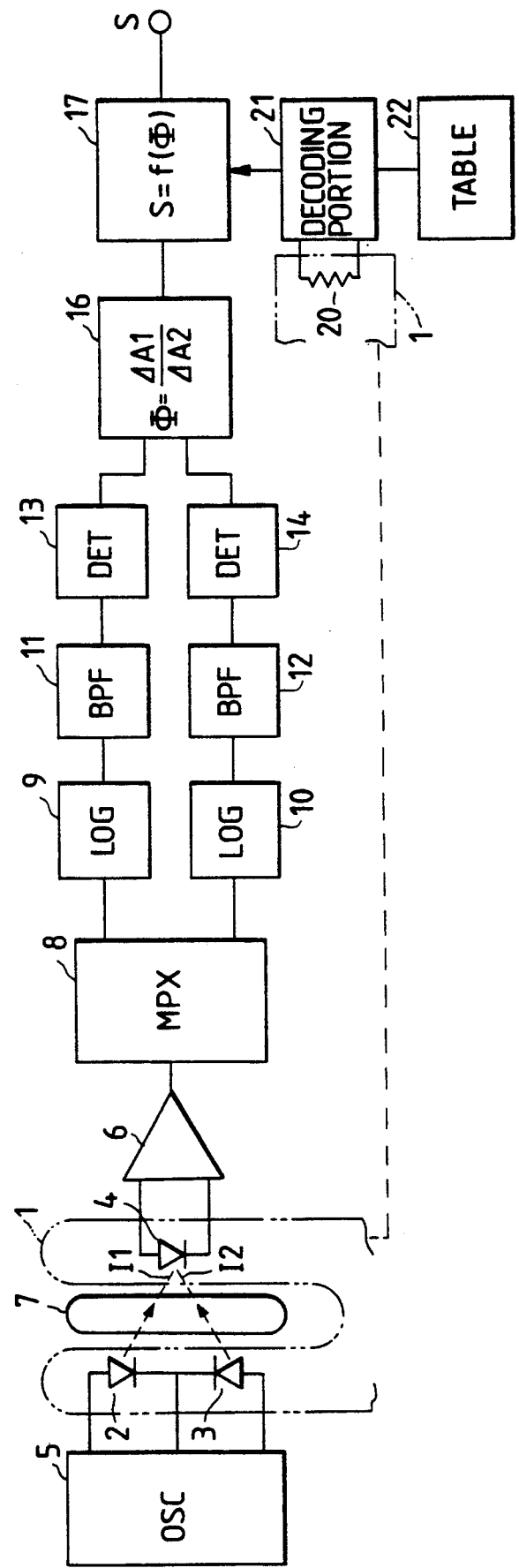
FIG. 5 is a block diagram showing the construction of a prior art pulse oximeter.

In FIG. 3, g0 denotes the graph for the reference wavelength 660 nm and g1, g2, g3 and g4 refer to the corresponding graphs for respective wavelengths of 650 nm, 665 nm and 670 nm.

If the pulsating component of absorbance at the wavelength 660 nm is written as $\Delta A1(660)$ and the pulsating component of absorbance at a certain wavelength as $\Delta A1(n)$, $\phi$ is equal to $\Delta A1/\Delta A2$ and, hence, eq. (1) can be written as:

$$\Delta A1(660)/\Delta A2 = An \cdot (\Delta A1(n)/\Delta A2) \tag{2}$$

Eliminating $\Delta A2$ from eq. (2), $\Delta A1(660)$ is given by:
$$\Delta A1(660) = An \cdot \Delta A1(n) \tag{3}$$

As is clear from eq. (3), A1(660), or the pulsating component of absorbance for the known reference wavelength 660 nm can be determined by multiplying the value of $\Delta A1(n)$, which is the pulsating component of absorbance that has been detected when red light has a certain wavelength offset from the reference wavelength 660 nm, by an appropriate coefficient An. On the basis of the computed value of $\Delta A1(660)$ and the value of $\Delta A2$, or the component of pulsation in the absorbance of infrared light, $\phi(660)$, or the absorbance ratio corresponding to the case where red light has the reference wavelength 660 nm can be determined by the following equation:

$$\phi(660) = \Delta A1(660)/\Delta A2 \tag{4}$$

Using the thus determined value of $\phi(660)$ (which is hereunder designated simply as $\phi$), the oxygen saturation S may be computed by the following equation, whereupon the oxygen saturation S that has been corrected for any variations in the emission wavelength of the red LED 2 and which corresponds exactly to the standard wavelength 660 nm is determined:

$$S = f(\phi) \tag{5}$$

The pulse oximeter of the present invention has been proposed to implement the method of correction described above, more specifically, specific embodiments of the pulse oximeter of the present invention are described below with reference to FIGS. 1 and 2.

The block diagram in FIG. 1 shows the basic construction of the pulse oximeter. As shown, a probe 1 contains in it a light-emitting diode 2 emitting red light, a light-emitting diode 3 emitting infrared light, and a light-receiving device 4 such as a photodiode that faces the light-emitting diodes 2 and 3. When a signal cable extending from the probe 1 is connected to the main body of the pulse oximeter, an oscillator (OSC) 5 on the main body is connected to the light-emitting diodes 2 and 3 whereas an amplifier 6 is connected to the light-receiving device 4. The light-emitting diode 2 provides the first light source for emitting red light at a reference wavelength which may be set at 660 nm, and the light-emitting diode 3 provides the second light source for emitting infrared light at a reference wavelength which may be set at 940 nm. When the probe 1 is attached to the tip of a finger of a subject or one of his earlobes, the living tissue 7 including the arterial blood stream will be situated between each of the light-emitting diodes 2 and 3 and the light-receiving device 4.

An oscillator 5 is coupled to the light-emitting diodes 2 and 3 so that red light and infrared light having different wavelengths will be alternately applied as pulses to the living tissue 7. Outputs of transmitted light I1 and I2, which remain after light scattering and absorption by the living tissue 7, are received alternately by the light-receiving device 4 and amplified by the amplifier 6 before they are sent to a multiplexer (MPX) 8. In synchronism with the oscillator 5, the multiplexer 8 feeds the output of the transmitted red light I1 to a logarithmic amplifier 9 whereas it feeds the output of transmitted infrared light I2 to a logarithmic amplifier 10.

The logarithmic amplifiers (LOG) 9 and 10 determine the absorbances of red light and infrared light, which are respectively passed through bandpass filters (BPF) 11 and 12 in the next stage, whereupon the pulsating components of the absorbances are respectively sent to detectors (DET) 13 and 14. The detectors 13 and 14 compose the first computing means, in which the difference between the peak and the bottom of each signal waveform is detected to determine $\Delta A1$, or, the pulsating component of absorbance at the wavelength of the red light, and $\Delta A2$, or the pulsating component of absorbance at the wavelength of the infrared light.

The detected value of $\Delta A1$ is sent to a multiplier 15 in the next stage and multiplied by coefficient An in accordance with the following equation, so that it is corrected to the value of $\Delta A1(660)$ which is detected when using the standard wavelength 660 nm:

$$\Delta A1(660) = An \cdot \Delta A1 \qquad (6)$$

In eq. (6), the coefficient An is the value that is predetermined in accordance with the characteristics of the red LED 2 in the probe 1 and it may be loaded as the value of a resistor or the like in the probe 1.

The value of $\Delta A1(660)$ computed in the multiplier 15 and the value of $\Delta A2$ delivered as output from the detector 14 are both sent to a second computing means 16, $\phi$, or the ratio between the pulsating components of absorbances for the wavelengths of red and infrared light, is computed by the following equation:

$$\phi = \Delta A1(660)/\Delta A2 \qquad (7)$$

The thus determined value $\phi$ of is approximate to $\phi(660)$, or the ratio between the pulsating components of absorbances for two wavelengths, one of which is 660 nm as the standard wavelength of red light. If this value of $\phi$ is used by a third computing means 17 in the next stage that performs an arithmetic operation for determining the oxygen saturation S by the following equation, one can obtain at an output terminal 19 the correct value of oxygen saturation S which has been corrected for any variations in the emission wavelength of the red LED 2:

$$S = f(\phi) \qquad (8)$$

It should be noted here that the multiplier 15 provides a gain adjusting means which insures that the value of $\Delta A1$ as obtained from the detector 13 is corrected to the value of $\Delta A1(660)$ which is obtained when using the standard wavelength 660 nm.

We now describe the construction of a more concrete example of the pulse oximeter with reference to FIG. 2. In this embodiment, a resistor R2 having a resistance that can provide information on the above-described coefficient An (the resistance is also designated by R2) is installed in the probe 1. The resistance of resistor R2 is such that when the emission wavelength of the red LED 2 in the probe 1 is measured in the process of probe fabrication, the probe will provide information on the coefficient An which is in one-to-one correspondence with the measured value of wavelength.

When a signal cable extending from the probe 1 is connected to the main body of the pulse oximeter, the resistor R2 which provides information on the coefficient An is connected to a multiplier 15. The multiplier 15 is so composed that the output terminal of the detector 13 is connected via resistor R1 (the resistance is also designated by R1) to the inverting input terminal of differential amplifier 18 which is part of the multiplier 15 whereas the resistor R2 on the probe side which provides information on the coefficient An is connected between the input and output terminals of the differential amplifier 18. The non-inverting input terminal of the differential amplifier 18 is grounded. In the multiplier 15, R2/R1 provides the value of coefficient An. The output terminal of the differential amplifier 18 is connected to the input terminal of the second computing means 16.

It should be noted here that the resistor R1, the resistor R2 in the probe 1 and the differential amplifier 18 compose a gain adjusting means which insures that the value of $\Delta A1$ from the detector 13 is corrected to the value for red light having the known standard wavelength 660 nm.

Being constructed in the manner described above, the pulse oximeter is operated in such a way that when the resistor R2 which provides information on the coefficient An is connected to the multiplier 15 from the probe side, the multiplier 15 multiplies the value of $\Delta A1$ from the detector 13 by the coefficient An and the corrected value of $\Delta A1(660)$ can be picked up from the output terminal of the multiplier 15.

In the computing means 16, the absorbance ratio $\phi$ is computed on the basis of the computed value of $\Delta A1(660)$ and the value of $\Delta A2$ from the detector 14 and this output of the computing means 16 is delivered to the computing means 17 in the next stage. Using the computed value of $\phi$, the computing means 17 performs an arithmetic operation for determining the oxygen saturation S and delivers at the output terminal 19 the value of oxygen saturation S which has been corrected for any variations in the emission wavelength of the red LED 2. The output oxygen saturation S is shown on the display.

The multiplying section and the various computing sections of the pulse oximeters shown in FIGS. 1 and 2 may be implemented not by analog circuits but by processing with a CPU (central processing unit).

In the embodiment described above, the optical outputs I1 and I2 of the light that has been transmitted through the living tissue 7 are detected to determine $\Delta A1$ and $\Delta A2$ which are the pulsating components of absorbances for two wavelengths. If desired, the outputs of reflected light that remains after attenuation by illumination of the living tissue 7 may be detected with the detecting device 4 to determine $\Delta A1$ and $\Delta A2$.

As described on the foregoing pages, the present invention is characterized in that $\Delta A1$ which is the pulsating component of absorbance that is detected when using red light of a certain wavelength is multiplied by the appropriate coefficient An and this insures that the detected value of $\Delta A1$ can be corrected to another value of $\Delta A1$, or the pulsating component of absorbance that is detected when using the reference wavelength of red light; as a consequence, the oxygen saturation S can be measured with the variations in the wavelength of red light being corrected to fall within the range of errors that are tolerable for practical purposes.

The necessary correction can be implemented with a simple circuit that causes the gain of $\Delta A1$ to vary with the wavelength of red light. If a resistor that determines the gain is installed in the probe, the conventional encoding and decoding operations which consist of imparting wavelength information and then determining the correction coefficient can be obviated, so that the procedure of processing operations for determining the oxygen saturation S can be simplified greatly. This may be considered to be equivalent to the case where the result of decoding is already incorporated as the value of a resistor in the probe and one only need connect the resistor in the probe to the correcting circuit so that the oxygen saturation is immediately delivered as an output.

Hence, the pulse oximeter of the present invention offers the advantage that its main body does not have to be equipped with a table that has written in it the values of wavelength and the coefficients of correction that are necessary for performing the decoding operation after wavelength information is red out of the probe and this contributes to a substantial simplification of the circuit configuration of the system. As a result, the precision of measurement with the pulse oximeter and its reliability can be enhanced while, at the same time, the production cost of the oximeter can be reduced.

What is claimed is:

1. A pulse oximeter comprising:
   a probe adapted to be attached to an organism, said probe including:
   a first light source for illuminating a living tissue of said organism including an arterial blood stream with a first light of a first predetermined wavelength;
   a second light source for illuminating said living tissue of said organism including said arterial blood stream with a second light of a second predetermined wavelength; and
   light receiving means for detecting optical outputs of said first and second lights which pass through and are not absorbed by said tissue of said organism;
   first computing means, responsive to detection outputs of said light receiving means, for computing pulsating components of absorbance of said first light and said second light due to said arterial blood stream based on said detection outputs of said light receiving means;
   gain adjusting means for multiplying a first output of said first computing means by a coefficient to compensate for differences between the first predetermined wavelength of said first light and a predetermined reference wavelength so as to produce a gain-adjusted value;
   second computing means, responsive to a second output of said first computing means and said gain-adjusted value, for computing an absorbance ratio based on said second output of said first computing means and said gain-adjusted value; and
   third computing means for computing an oxygen saturation of arterial blood on a basis of said absorbance ratio delivered from said second computing means.

2. A pulse oximeter as claimed in claim 1, wherein said gain adjusting means comprises:
   a resistor disposed in said probe having a value of resistance corresponding to said coefficient; and
   a multiplier coupled to said resistor for multiplying said first output of said first computing means by said coefficient.

3. A pulse oximeter as claimed in claim 1, wherein said first light source is a red light source.

4. A pulse oximeter as claimed in claim 1, wherein said predetermined reference wavelength is substantially 660 nm.

5. A pulse oximeter as claimed in claim 1, wherein said second light source is an infrared source.

* * * * *